United States Patent
Wu et al.

(10) Patent No.: US 12,358,902 B2
(45) Date of Patent: Jul. 15, 2025

(54) 5-(2,5-BIS(4-CHLORO-2-ISOPROPYLPHENYL) THIOPHEN-3-YL)-1H-TETRAZOLE FOR THE TOPICAL TREATMENT OF BACTERIAL INFECTIONS

(71) Applicant: DENOVAMED INC., Toronto (CA)

(72) Inventors: Fan Wu, Toronto (CA); Christopher R. McMaster, Toronto (CA); Donald F. Weaver, Toronto (CA)

(73) Assignee: Denovamed Inc., Toronto (CA)

( * ) Notice: Subject to any disclaimer, the term of this patent is extended or adjusted under 35 U.S.C. 154(b) by 217 days.

(21) Appl. No.: 16/767,664

(22) PCT Filed: Dec. 10, 2018

(86) PCT No.: PCT/CA2018/051572
§ 371 (c)(1),
(2) Date: May 28, 2020

(87) PCT Pub. No.: WO2019/113684
PCT Pub. Date: Jun. 20, 2019

(65) Prior Publication Data
US 2020/0369653 A1    Nov. 26, 2020

Related U.S. Application Data

(60) Provisional application No. 62/597,159, filed on Dec. 11, 2017.

(51) Int. Cl.
*C07D 409/04* (2006.01)
*A61P 17/02* (2006.01)
*A61P 31/04* (2006.01)

(52) U.S. Cl.
CPC ............ *C07D 409/04* (2013.01); *A61P 17/02* (2018.01); *A61P 31/04* (2018.01)

(58) Field of Classification Search
CPC ........ C07D 409/04; A61P 17/02; A61P 31/04; A61K 31/41; A61K 8/49; A61Q 17/005; A61Q 19/06
See application file for complete search history.

(56) References Cited

U.S. PATENT DOCUMENTS

2010/0076028 A1 * 3/2010 Wu .................... A61K 31/4439
514/340

FOREIGN PATENT DOCUMENTS

| CA | 2603534 | 2/2014 | |
|---|---|---|---|
| CA | 2828748 | 6/2019 | |
| WO | WO 2012/116452 A1 * | 9/2012 | ........... C07D 409/04 |

* cited by examiner

*Primary Examiner* — Joseph K McKane
*Assistant Examiner* — David M Shim
(74) *Attorney, Agent, or Firm* — Michael R. Williams; Ryan W Dupius; Ade & Company Inc.

(57) ABSTRACT

A compound 5-(2,5-bis(4-chloro-2-isopropylphenyl)thiophen-3-yl)-1H-tetrazole, methods for the manufacture of said compound, topical compositions comprising said compound and methods of use thereof in the topical treatment of infections caused by pathogenic bacteria at a wound site.

12 Claims, 2 Drawing Sheets

5-(2,5-BIS(4-CHLORO-2-ISOPROPYLPHENYL)THIOPHEN-3-YL)-1H-TETRAZOLE FOR THE TOPICAL TREATMENT OF BACTERIAL INFECTIONS

PRIOR APPLICATION INFORMATION

The instant application is a 371 of PCT Application CA2018/051572, filed Dec. 10, 2018, which claimed the benefit of U.S. Provisional Patent Application Ser. No. 62/597,159, filed Dec. 11, 2017, entitled "Topical Treatment of Infections", the contents of which are incorporated herein by reference.

BACKGROUND OF THE INVENTION

Diabetes is a critical disease affecting over 415 million people worldwide, with the incidence expected to rise to over 642 million by 2035 (International Diabetes Federation, 2016). Diabetic patients can present with numerous serious complications which include reduced peripheral blood flow. Reduced blood flow to the extremities can result in the onset of peripheral neuropathy, the degeneration of peripheral nerves. Affecting up to 50% of diabetics, peripheral neuropathy is typified by a sensation of tingling, numbness and the inability to detect pain in extremities, which results in infections that develop into diabetic ulcers (so-called "diabetic ulcer infections" or "DUIs"), often found on the foot ("DFIs"). Each year, approximately 3% of diabetics develop a diabetic ulcer, which translates to over 11.5 million people. A significant proportion of diabetic ulcer patients develop serious infections that reach the deeper layers of the skin and ultimately into the bone, often resulting in partial or full amputation of the extremity. As a result of the poor treatment options currently available many such infections progress in severity.

Current antibiotic treatments for DUIs have limited success as ~50% transition from DFI Stage 2 to DFI Stage 3. The most severe cases (representing up to 50% of all diabetic foot infections) require full or partial amputation of the foot, indeed DFIs account for 25% of all diabetic patient hospital admissions. Existing oral or injectable antibiotics have not been effective to treat DFIs, because the vasculature in and around the diabetic ulcer is poor and reduces the ability of such antibiotics to reach the site of infection.

Topical antibiotics hold promise to provide more effective treatment, as they are applied directly to the site of infection and can eradicate bacteria even in the absence of normal vasculature. Unfortunately, currently available topical antibiotics are generally not effective, due to their inherent physicochemical properties that prevent them from penetrating deep into the skin. Additionally, multi-drug resistance (MDR) has been exhibited within DFIs, adding to the challenge of designing appropriate therapies.

Recent strategies to develop new antibiotics to target MDR bacteria have largely centered on creating new generations of existing antibiotics versus known targets. However, as underlying mechanisms are already in place resistance often develops quickly. Classes of antibiotics not currently being used, designed versus novel targets, are needed as they hold greater promise to combat MDR bacterial infections.

SUMMARY OF THE INVENTION

Compounds are provided that have physiochemical properties tailored for topical administration and that inhibit a bacterial target not currently exploited in antibacterial therapy. These compounds demonstrate a bacterial spectrum and efficacy in topical administration that are unexpectedly good even as compared to antibacterial compounds in a similar class.

In general, in an aspect, 5-(2,5-bis(4-chloro-2-isopropylphenyl)thiophen-3-yl)-1H-tetrazole or a pharmaceutically acceptable salt thereof are provided.

In general, in an aspect, a pharmaceutical composition having 5-(2,5-bis(4-chloro-2-isopropylphenyl)thiophen-3-yl)-1H-tetrazole or a pharmaceutically acceptable salt thereof, and a dermatologically acceptable carrier is provided.

In general, in an aspect, the use of the above compositions as a medicament is provided, particularly as a medicament for eradicating pathogenic bacteria within a diabetic ulcer or for treatment of a diabetic foot infection or for cellulitis.

In general, in an aspect, a method of eradicating pathogenic bacteria within a diabetic ulcer is provided, the method including applying an effective amount of one of the above compositions upon the ulcer of an individual in need of such treatment.

In general, in an aspect, a method of treatment of diabetic foot infection of an individual in need of such treatment at a site of infection is provided, the method including applying an effective amount of one of the above compositions on the site of infection.

In general, in an aspect, a method of treatment of cellulitis at a site of infection of an individual in need of such treatment is provided, the method including applying an effective amount of one of the above compositions on the site.

In general, in an aspect, a method of manufacture of 5-(2,5-bis(4-chloro-2-isopropylphenyl)thiophen-3-yl)-1H-tetrazole or a pharmaceutically acceptable salt thereof is provided, the method including reacting a mixture of N-protected 5-bromotetrazoles with thiophen-3-ylboronic acid under palladium cross-coupling conditions.

With the foregoing and other advantages and features of the invention that will become hereafter apparent, the nature of the invention may be more clearly understood by reference to the following detailed description of the invention and the appended claims.

DETAILED DESCRIPTION OF THE INVENTION

Lipid synthesis is an attractive target for antibacterial drug discovery as many steps are unique to bacteria and are highly conserved across Genera. AcpS, which catalyzes the activation of acyl carrier protein for its subsequent use in the synthesis of lipids and other important macromolecules, is one such target. We herein disclose an AcpS inhibitor, 5-(2,5-bis(4-chloro-2-isopropylphenyl)thiophen-3-yl)-1H-tetrazole, that is effective against a wide range of clinically relevant Gram positive bacteria. Due to its unique mode of action, 5-(2,5-bis(4-chloro-2-isopropylphenyl)thiophen-3-yl)-1H-tetrazole shows a high level of potency versus important MDR clinical isolates of MRSA and VRE. Topical treatment of animals with 5-(2,5-bis(4-chloro-2-isopropylphenyl)thiophen-3-yl)-1H-tetrazole eradicates MRSA infection and improves healing. 5-(2,5-bis(4-chloro-2-isopropylphenyl)thiophen-3-yl)-1H-tetrazole therefore has value as a medicament for topical infections.

Specifically, as discussed herein, the unique mode of action is that the compound is an ACP synthase inhibitor as discussed in the Examples. In addition, the compound has been shown to have particularly good penetration into skin layers without appreciably penetrating through the skin into the systemic space. As will be appreciated by one of skill in the art, this is a significant benefit because the drug is present where the bacteria are (in the skin) but would not be expected to enter into the body, as discussed below.

All patents, patent applications, and other publications referred to herein are hereby incorporated by reference in their entireties.

In an embodiment, 5-(2,5-bis(4-chloro-2-isopropylphenyl)thiophen-3-yl)-1H-tetrazole or a pharmaceutically acceptable salt thereof are provided.

In an embodiment, a pharmaceutical composition comprising 5-(2,5-bis(4-chloro-2-isopropylphenyl)thiophen-3-yl)-1H-tetrazole or a pharmaceutically acceptable salt thereof, and a dermatologically acceptable carrier is provided. In some embodiments, the dermatologically acceptable carrier is a cream and the 5-(2,5-bis(4-chloro-2-isopropylphenyl)thiophen-3-yl)-1H-tetrazole or a pharmaceutically acceptable salt thereof is present at a concentration of about 0.5-5%, for example, of 2% or 1%. In some embodiments, the dermatologically acceptable carrier comprises GLAXAL BASE™ (Emollient Cream).

In an embodiment, the use of one of the above provided compositions as a medicament is provided. In some embodiments, the medicament is for eradicating pathogenic bacteria within a diabetic ulcer. In some embodiments, the medicament is for treatment of a diabetic foot infection. In some embodiments, the medicament is for treatment of cellulitis.

Examples of pathogenic bacteria include but are by no means limited to: *Enterococcus* sp., *Enterococcus faecalis*, including vancomycin resistant *enterococcus* ATCC700211 and ATCC51299, *Bacillus* sp., *Bacillus cereus*, *Staphylococcus* sp., *Staphylococcus epidermidis*, *Staphylococcus aureus*, *Staphylococcus aureus* strains NRS7 (vancomycin intermediate), NRS2 (vancomycin intermediate), ATCC43300 (methicillin resistant-MRSA), NRS1, NRS382 (USA100 epidemic strain), NRS383 (USA200 epidemic strain), NRS384 (USA300 epidemic strain), clinical isolates including MRSA clinical isolates, community-acquired MRSA clinical isolates, and multi-drug resistant (MDR) ciprofloxacin, penicillin, erythromycin and/or mupirocin resistant clinical isolates, *Streptococcus* sp., *Streptococcus agalactiae*, *Streptococcus pneumoniae* and *Clostridium* spp.

In an embodiment, a method of eradicating pathogenic bacteria within a diabetic ulcer is provided, the method comprising applying an effective amount of one of the above provided compositions upon the ulcer of an individual in need of such treatment.

In an embodiment, a method of treatment of diabetic foot infection at a site of infection is provided, the method comprising applying an effective amount one of the above provided compositions on the infection site of an individual in need of such treatment.

In an embodiment, a method of treatment of cellulitis at a site of infection is provided, the method comprising applying an effective amount of one of the above provided compositions on the infection site of an individual in need of such treatment.

As will be appreciated by one of skill in the art, an "individual in need of such treatment" refers to an individual who is suffering from, has been diagnosed with or is suspected of having a diabetic ulcer comprising pathogenic bacteria, a diabetic foot infection and/or cellulitis.

As will be appreciated by one of skill in the art, an "effective amount" refers to an amount that is sufficient to reduce the severity of at least one symptom associated with a diabetic ulcer comprising pathogenic bacteria, a diabetic foot infection and/or cellulitis. Examples of symptoms of these diseases are well known to one of skill in the art and/or can be determined easily by consultation with a variety of reference sources. For example, some symptoms include: inflammation and purulence, continuation of ulcerative condition (lack or slowness of healing), increase in ulcer area or depth.

In some embodiments, an "effective amount" is an amount effective to clear the infection or an amount effective to reduce the risk of complications such as osteomyelitis or lower extremity amputation.

In use, the compound should be applied periodically, for example, once or twice daily. Common applications would be for 7-14 days, for example, for 7 or 10 or 14 days or until wound closure.

In an embodiment, a method of manufacture of manufacture of 5-(2,5-bis(4-chloro-2-isopropylphenyl)thiophen-3-yl)-1H-tetrazole or a pharmaceutically acceptable salt thereof is provided, the method comprising reacting a mixture of N-protected 5-bromotetrazoles with thiophen-3-yl-boronic acid under palladium cross-coupling conditions. In some embodiments, the nitrogen protecting group is benzyl. In some embodiments, the palladium cross-coupling conditions comprise $Pd(PPh_3)_4$ and sodium carbonate.

Methods of treatment or uses as provided above are preferably applied to a mammal, more preferably a human, in need thereof. Method of treatment or uses are preferably administered topically in, on, or around the ulcer or site of infection as applicable.

Definitions

Unless otherwise defined, terms as used in the specification refer to the following definitions, as detailed below.

The terms "administration" or "administering" compound should be understood to mean providing 5-(2,5-bis(4-chloro-2-isopropylphenyl)thiophen-3-yl)-1H-tetrazole or a pharmaceutically acceptable salt thereof to an individual in a form that can be introduced into or onto that individual's body in an amount effective for prophylaxis, treatment, or diagnosis, as applicable; and particularly, providing topical dosage forms that comprise pharmaceutically acceptable carriers, more particularly that comprise dermatologically acceptable carriers.

In some embodiments, topical dosage forms are liquid, solid, or semisolid. In some embodiments, topical dosage forms are formulated as creams, emulsions, ointments, pastes, or gels. In some embodiments, the topical dosage form is applied to the skin of an individual, whether open or closed. In some embodiments, a topical formulation is mixed with 5-(2,5-bis(4-chloro-2-isopropylphenyl)thiophen-3-yl)-1H-tetrazole or a pharmaceutically acceptable salt thereof under sterile conditions, the topical formulation comprising pharmaceutically acceptable carriers and any desired excipients such as preservatives, antioxidants, buffers, humectants, permeation enhancers, or thickeners. In some embodiments, the formulation comprises an oleaginous or hydrocarbon base. In some embodiments, the formulation comprises an anhydrous or absorption base. In some embodiments, the formulation comprises an emulsion base (water-in-oil or oil-in-water). In some embodiments, the formulation comprises a water-soluble base.

The term "amino" as used herein means a —NH$_2$ group.

The term "bromo" as used herein means —Br.

The term "carbonyl" as used herein means a —C(=O)— group.

The term "carboxy" as used herein means a —COOH group, which may be protected as an ester group: —COO-alkyl.

The term "cyano" as used herein means a —CN group.

The term "fluoro" as used herein means —F.

The term "halo" or "halogen" as used herein means Cl, Br, I, or F.

The term "hydroxy" as used herein means an —OH group.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, CH$_2$I$_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by (alkyl-O)2C=O, a diaryl anhydride, for example as represented by (aryl-O)2C=O, an acyl halide, an alkylchloroformate, or an alkylsulfonylhalide, an arylsulfonylhalide, or halo-CON(alkyl) 2, for example acetylchloride, benzoylchloride, benzylbromide, benzyloxycarbonylchloride, formylfluoride, phenylsulfonylchloride, pivaloylchloride, (tert-butyl-O—C=O) 2 O, trifluoroacetic anhydride, and triphenylmethylchloride.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., Protective Groups in Organic Synthesis (3 rd ed., John Wiley & Sons: 1999); Larock, R. C., Comprehensive Organic Transformations (2 nd ed., John Wiley & Sons: 1999). Some examples include benzyl, diphenylmethyl, trityl, Cbz, Boc, Fmoc, methoxycarbonyl, ethoxycarbonyl, and pthalimido. Protecting groups include, for example, nitrogen protecting groups and hydroxy-protecting groups. A compound protected at a nitrogen can be referred to as being "N-protected".

The compounds of the invention can be used in the form of pharmaceutically acceptable salts derived from inorganic or organic acids. Pharmaceutically acceptable salt(s) are well-known in the art. For clarity, the term "pharmaceutically acceptable salts" as used herein generally refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., Remington's Pharmaceutical Sciences, 18 th ed. (Mack Publishing, Easton Pa.: 1990) and Remington: The Science and Practice of Pharmacy, 19 th ed. (Mack Publishing, Easton Pa.: 1995). The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

Certain compounds of the present invention may be isotopically labelled, e.g., with various isotopes of carbon, fluorine, or iodine, as applicable when the compound in question contains at least one such atom.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, for example, the two phrases "XOH, wherein X is pyridyl" and "XOH, wherein X is pyridine" are accorded the same meaning, and encompass the compounds pyridin-2-ol, pyridin-3-ol and pyridin-4-ol.

Unless otherwise indicated, the terms "prevent," "preventing" and "prevention" contemplate an action that occurs before a patient begins to suffer from the specified disease or disorder, which inhibits or reduces the severity of the disease or disorder or of one or more of its symptoms. The terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound is an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a "diagnostically effective amount" of a compound is an amount sufficient to diagnose a disease or condition. In general, administration of a compound for diagnostic purposes does not continue for as long as a therapeutic use of a compound, and might be administered only once if such is sufficient to produce the diagnosis.

Unless otherwise indicated, a "therapeutically effective amount" of a compound is an amount sufficient to treat a disease or condition, or one or more symptoms associated with the disease or condition.

The term "subject" is intended to include living organisms in which disease may occur. Examples of subjects include humans, monkeys, cows, sheep, goats, dogs, cats, mice, rats, and transgenic species thereof.

The term "substantially pure" means that the isolated material is at least 90% pure, preferably 95% pure, even more preferably 99% pure as assayed by analytical techniques known in the art.

Actual dosage levels of active ingredients in pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

An effective amount of 5-(2,5-bis(4-chloro-2-isopropylphenyl)thiophen-3-yl)-1H-tetrazole can be employed in pure form or, where such forms exist, in pharmaceutically acceptable salt form. The total daily usage will be decided by an attending physician within the scope of sound medical judgment. The specific effective dose level and frequency of administration for any particular patient will depend upon a variety of factors including the disorder being treated and the severity of the disorder; the specific composition employed; the age, body weight, general health, sex and diet of the patient; the time required for administration; the duration of effect of each administration; the duration of the overall treatment; the risk/benefit ratio; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

Further information about the compounds, compositions, methods, and uses described herein can be found in the Examples below.

EXAMPLES

Example 1—Synthesis of 5-(2,5-bis(4-chloro-2-isopropylphenyl)thiophen-3-yl)-1H-tetrazole Reference is made to the chemical scheme given below:

Bromocarbonitrile 2 (1.0 g, 3.7 mmol), isopropylphenylboronic ester 1 (2.31 g, 8.2 mmol, 2.2 eq), and Pd(PPh$_3$) 4 (0.22 g, 0.19 mmol, 0.05 eq) were added to a round bottom flask, and vacuumed for 3 sec and flushed with argon three times. To this was added 2M aq. sodium carbonate solution

(9.4 ml, 18.8 mmol, 5 eq) and 20 ml dioxane. The reaction was stirred at 95° C. overnight then quenched with water. The dark mixture was extracted with ethyl acetate (2×20 ml), dried over anhydrous sodium sulphate, filtered, and concentrated via rotary evaporation. Thiophenylcarbonitrile 3 (1.4 g, 90%) was obtained by flash column chromatography (25% DCM in hexanes).

Thiophenylcarbonitrile 3 (1.0 g, 2.4 mmol), sodium azide (0.39 g, 6.0 mmol, 2.5 eq), and zinc bromide (1.36 g, 6.0 mmol, 2.5 eq) were combined with 20 ml anhydrous DMF in a in a round bottom flask, and vacuumed for 3 sec and flushed with argon three times. The reaction was stirred at 135° C. overnight then quenched with 5 ml 1 N HCl solution. The mixture was filtered and the product was obtained by flash column chromatography (1% AcOH and 35% EtOAc in hexanes).

NMR evaluation. $^1$H NMR (500 MHz, CDCl$_3$): δ (ppm) 1.13 (s, br, 6H), 1.30 (d, J=6.8 Hz, 6H), 2.92 (m, 1H), 3.38 (m, 1H), 7.26 (dd, J=2.0, 8.1 Hz, 1H), 7.40 (m, 4H), 7.54 (d, J=1.3 Hz, 1H), 7.76 (s, 1H); $^{13}$C NMR (125 MHz, CDCl$_3$): δ (ppm) 24.6 (2), 24.7, 24.8, 30.4, 31.0, 123.0, 126.5, 126.9, 127.2, 127.8, 128.1, 128.7, 130.0, 132.5, 132.7, 135.9, 137.8, 142.5, 143.9, 150, 151.5.

Example 2 (Prophetic)—Azide-free synthesis of 5-(2,5-bis(4-chloro-2-isopropylphenyl)thiophen-3-yl)-1H-tetrazole 5-(2,5-bis(4-chloro-2-isopropylphenyl)thiophen-3-yl)-1H-tetrazole can also be made by protection of tetrazole to yield a mixture of N-protected tetrazoles. This step is followed by bromination to yield a mixture of N-protected 5-bromotetrazoles, followed by palladium cross-coupling using thiophen-3-ylboronic acid. The resulting products are then brominated at the 2- and 5-positions of thiophene, followed by palladium cross-coupling using (4-chloro-2-isopropylphenyl)boronic acid. Deprotection of the N-protected tetrazole moieties resolves the mixture into a single product. Deprotection can be combined or followed with the introduction of pharmaceutically acceptable salt moieties using methods known in the art. One possible synthesis is given in the scheme below, in which the nitrogen protecting group is benzyl:

Example 3—Preparation of a pharmaceutical composition containing 5-(2,5-bis(4-chloro-2-isopropylphenyl)thiophen-3-yl)-1H-tetrazole and a dermatologically acceptable carrier Formulation was performed by dissolving 50 mg of compound in 50 µl of 100% DMSO, followed by gradual addition and mixing to 5 ml GLAXAL BASE™ (Emollient Cream) (WellSpring Pharmaceutical Canada Corp., Oakville, Canada) to give a final concentration of 1% (w/v) compound and 1% (v/v) DMSO.

Biological Data

Minimum Inhibitory Concentrations (MIC)

Using a broth microdilution assay according to Clinical Laboratory Standards Institute (CSLI) guidelines, we tested 5-(2,5-bis(4-chloro-2-isopropylphenyl)thiophen-3-yl)-1H-tetrazole ("Test Article" in below table) to establish MICs against a broad range of MDR bacteria and noted substantive activity versus methicillin-resistant *Staphylococcus aureus* (MRSA), vancomycin-resistant *Enterococcus* (VRE) and *Streptococcus* spp. Antimicrobial susceptibility testing was performed by a microdilution broth assay according to CLSI guidelines. The inoculum was prepared from stationary-phase cultures diluted in water. Microtiter plate wells received aliquots of 100 µL of the compound diluted in Mueller-Hinton II cation adjusted media. The final concentration of compound typically ranged from 250 to 0.125 µg/ml in serial two-fold dilutions. In addition to the test compound, growth and sterility controls were included, along with DMSO vehicle control rows. The microtiter plates were inoculated with $5 \times 10^5$ bacteria and incubated overnight at 35° C. in a humidified atmosphere.

Further in vitro testing of 5-(2,5-bis(4-chloro-2-isopropylphenyl)thiophen-3-yl)-1H-tetrazole versus a panel of 125 important Gram positive strains and MDR clinical isolates of MRSA, VRE, and *S. epidermidis* indicated MIC values of 0.5-1.0 µg/ml against these MDR strains, including strains resistant to vancomycin, penicillin, erythromycin and ciprofloxacin.

| Organism and properties | Test Article | vancomycin |
|---|---|---|
| | Antibacterial activity (MIC, µg/ml) | |
| *E. faecium* ATCC51299 vancomycin resistant | 1.0 | >16 |
| *E. faecalis* ATCC51599 vancomycin resistant | 0.5 | >16 |
| *S. epidermidis* NRS7 vancomycin intermediate | 1.0 | 4.0 |
| *S. aureus* MRSA USA300 epidemic strain | 0.5 | 1.0 |
| *S. aureus* MRSA USA200 epidemic strain | 0.5 | 0.5 |
| *S. aureus* MRSA USA100 epidemic strain | 1.0 | 1.0 |
| *S. aureus* MRSA MISA MU50 NRS1 | 0.5 | 4.0 |
| *S. aureus* MRSA MISA MU3 NRS2 | 1.0 | 1.0 |
| *S. aureus* MRSA ATCC43300 | 0.5 | 0.5 |
| *S. aureus* MRSA clinical isolate from Manchester | 0.5 | 0.5 |
| *S. aureus* MRSA clinical isolate ciprofloxacin resistant | 1.0 | 0.5 |
| *S. aureus* MRSA clinical isolate penicillin and erythromycin resistant | 0.5 | 1.0 |
| *S. aureus* MRSA clinical isolate multi resistant | 0.5 | 0.5 |

5-(2,5-bis(4-chloro-2-isopropylphenyl)thiophen-3-yl)-1H-tetrazole also retained activity against mupirocin resistant strains of *S. epidermidis, E. faecalis, E. faecalis* VRE, and in a panel of mupirocin resistant *S. aureus* strains (MMX 1013, MMX 7779, MMX 7782, MMX 8845, MMX 9202: 2 ug/ml MIC vs >256 ug/nl for nupitocin); this is notable since mupirocin is one of the more commonly used topical antibiotics.

5-(2,5-bis(4-chloro-2-isopropylphenyl)thiophen-3-yl)-1H-tetrazole also retained activity against *Clostridium* spp., a pathogen present in more advanced/complex DUI cases, while its structural isomer 5-(4,5-bis(4-chloro-2-isopropylphenyl)thiophen-2-yl)-1H-tetrazole was inactive against such species.

5-(2,5-bis(4-chloro-2-isopropylphenyl)thiophen-3-yl)-1H-tetrazole is rapidly bactericidal as demonstrated against USA100 and USA300 MRSA strains.

Mechanism of Action

The acpS gene was amplified from *S. aureus* and *E. coli* genomic DNA and inserted into a pET23b vector using standard recombinant DNA methodology such that the protein product would result in addition of a C-terminal 6×-His tag in frame with the AcpS open reading frames. The DNA sequence of the products inserted in the vector was sequenced and was found to be identical to the known *E. coli* and *S. aureus* acpS open reading frames. Recombinant His-Tagged AcpS expression was induced by IPTG addition and overnight culture. Cell lysate was obtained by sequential aspiration through 16, 18 and 21 G needles in a buffer of 50 mM Tris-HCl (pH 8.5), 10 mM MgCl2, 2 mM DTT, 5% glycerol, and further adjusted to pH 8.1 with MES. Purification via His-Tag methodology resulted in a stock purified enzyme solution of ~2 mg/ml. In a typical AcpS enzyme activity assay, 57 µM [$^3$H]-labeled acyl-CoA, 2 µg apo-ACP, 10 mM $MgCl_2$, 5 mM DTT, 50 mM Na phosphate (pH 7.0), and AcpS in a final volume of 10 µL were incubated at room temperature in a 1.5 mL microcentrifuge tube. At 5, 10, 15, and 20 minutes 2 µL of reaction were added to 750 µL 10% TCA on ice. Bovine serum albumin (BSA; 20 µl of a 25 mg/ml solution) was then added to facilitate precipitation of radiolabeled protein. The samples were centrifuged at 12 000 rcf for 5 min. Supernatants were removed, and the pellets were rinsed twice with 750 µL of 10% trichloroacetic acid. Pellets were resuspended in 50 µL of formic acid and transferred to scintillation vials. 2 mL of scintillation fluid was added, and the amount of [$^3$H]-labeled holo-ACP formed was quantified by liquid scintillation counting. Each data point (remaining AcpS enzyme activity) was expressed as a percentage of vehicle control, with the median value of four time points presented.

AcpS was seen to be inhibited by 5-(2,5-bis(4-chloro-2-isopropylphenyl)thiophen-3-yl)-1H-tetrazole.

To determine if AcpS inhibition is the main in vivo target that results in bacterial killing by 5-(2,5-bis(4-chloro-2-isopropylphenyl)thiophen-3-yl)-1H-tetrazole, we over-expressed AcpS in bacteria. An *E. coli* strain genetically engineered to have a porous outer membrane (strain D22) was transformed with a plasmid expressing either *E. coli* or *S. aureus* AcpS under control of an IPTG inducible promoter. Compounds that kill bacteria through inhibition of AcpS should shift the MIC to a higher concentration upon increased AcpS expression, and that is indeed what was seen for 5-(2,5-bis(4-chloro-2-isopropylphenyl)thiophen-3-yl)-1H-tetrazole (32-fold for *E. coli;* 16-fold for *S. aureus*).

Selectivity in vitro enzyme assays, performed analogously to those described above, determined that 5-(2,5-bis(4-chloro-2-isopropylphenyl)thiophen-3-yl)-1H-tetrazole did not inhibit two other ACP utilizing bacterial enzymes: LpxA and fatty acid synthase.

Dermal Pharmacokinetics on Full Thickness Human Cadaver Skin

Full thickness human skin was taken from the torso of a post-mortem human donor and stores at −80 degrees Celsius. On the day of the study, skin pieces were thawed for at least minutes at room temperature in saline, then divided into individual pieces of approximately 2 cm length×2 cm width from which seven pieces of full thickness skin was selected. Approximately ⅔ of the width of the hypodermis layer was trimmed in order to mount the selected pieces into Franz cells. Receiver buffer was prepared (Krebs-Ringer bicarbonate buffer containing 10 mM HEPES, 15 mM sodium bicarbonate, and 1.2 mM calcium chloride; adjusted to pH 7.4 and fortified with 0.1% sodium azide and 1% bovine serum albumin). Each piece was equilibrated for 30 min with 12 mL of receiver buffer at 32 degrees Celsius by a water-jacket/stirring module running at 600 rpm. Transepithelial water loss was read for each piece after 30 mins using a vapometer. Exposed surface area of the piece was 1.77 square cm.

Approximately 300 ul of 5-(2,5-bis(4-chloro-2-isopropylphenyl)thiophen-3-yl)-1H-tetrazole formulated in 2% w/w GLAXAL BASE™ (Emollient Cream) was applied directly through syringe on top of each piece. Receiver samples were taken from the receiver compartment of each Franz cell at 3, 6, 12, 18, and 24 hours and replaced with an equal volume of fresh, warm buffer to maintain sink conditions. At the end of 24 hours, the bulk amount of formulation remaining on each piece of skin was wiped using cotton tips, stored together in a dry vial for analysis. Epidermis and dermis were then separated gently using forceps after a brief heat treatment at 60 degrees Celsius for no longer than 2 minutes. Each layer was then blotted dry, weighted and stored in separate glass vials. All samples were stored at −80 degrees Celsius until analysis by LC/MS-MS.

The cumulative concentrations of 5-(2,5-bis(4-chloro-2-isopropylphenyl)thiophen-3-yl)-1H-tetrazole that permeated at each time point were calculated by the sum of the measured concentration at that time point plus 1/12 of the measured concentrations at the previous time points (since 1 mL out of the 12 mL total receiver volume is withdrawn and replaced each time). The flux values over the course of the 24 hour permeation period were calculated from the slope of the linear portion of the curve. Flux was represented by the equation $$\text{Flux} = d[(C_{r\text{-}T} \times V_r)/dt/A$$

where $C_{r\text{-}T}$ is the cumulative concentration at each time point (ng/mL); $V_r$ is 12 mL; t is duration in hours; and A is the surface area of 1.77 square cm.

Results showed that there was no detectable 5-(2,5-bis(4-chloro-2-isopropylphenyl)thiophen-3-yl)-1H-tetrazole in the receiver samples at the end of the 24 hour permeation period (lower limit of detection: 0.5 ng/mL). Flux from the top (simulating topical administration) all the way through to the bottom (simulating entry into systemic space) was calculated to be less than 0.141 ng/hr/cm² in this experiment. Rather, 5-(2,5-bis(4-chloro-2-isopropylphenyl)thiophen-3-yl)-1H-tetrazole was found to accumulate in the layers of skin. Quantitation by LC-MS/MS showed levels in epidermis (163±58.0 ng per mg tissue), dermis (0.821±0.469 ng per mg tissue), and hypodermis (1.86±1.04 ng per mg tissue) at the end of the 24 hour permeation period.

Efficacy in Rabbit Ischemic Wound Model 5-(2,5-bis(4-chloro-2-isopropylphenyl)thiophen-3-yl)-1H-tetrazole was tested for its efficacy against infection in the rabbit ischemic wound model, the gold standard animal model mimicking human DUI. In this model, the ear is made ischemic by division of central and rostral nutrient arteries of New Zealand white rabbits. New Zealand White rabbits were employed for this study and their husbandry and experimental manipulation adhered to standard Guides for the Care and Use of Laboratory Animals (2001). An incision was made to the level of bare cartilage at the base of the ear and followed by injection intradermally with epinephrine to obtain vasoconstriction and aid with skin detachment. Skin is separated from the underlying perichondrium and removed with a 6.0 mm aortic biopsy punch. Food and water were given ad libidum and animals were acclimatized for 7 days with photoperiods of alternating 12 h light and dark provided, along with analgesic (BUPRENEX™ (buprenorphine) 0.02 mg/kg sc) and anaesthesia (isoflurane (0.5-5% with oxygen carrier 0.5-2 L/min) during procedures.

An ischemia wound healing model was conducted surgically. Each wound was inoculated with 50 µl of $2 \times 10^7$ CFU/ml MRSA (ATCC #33591) and dressed. After one day, wounds were treated with either 50 µl control cream containing vehicle (N=4), 50 µl containing mupirocin (N=4), or 50 µl cream containing 5-(2,5-bis(4-chloro-2-isopropylphenyl)thiophen-3-yl)-1H-tetrazole (N=8) daily. Clinical observations were performed on days 1, 3, 5, 7, 10 and 14. Wounds were assessed and observations recorded using the Draize scoring system. Digital photographs of each wound were obtained and documented.

On day 14 post-wounding, under anesthesia, the animals were euthanized with an intravenous injection of BEUTHANASIA-D™ (phenobarbital sodium and phenytoin sodium) at a dosage of 150 mg/kg of body weight. Specimens including the entire wound, along with approximately 2-3 mm of the normal unwounded skin margins were harvested. Each ear wound specimen was sectioned into halves. For one half of the wound, the wound was placed into a container with 10% neutral buffered formalin and processed for routine histological evaluation. Wound organization was scored for four parameters on a scale of 0-4 at the wound site for inflammation, granulation, angiogenesis, and epithelialization. Wounds were characterized in a blinded manner by a board certified member of the College of American Pathologists. The other half of the wound was weighed (mg) in a sterile Petri dish, then placed in a sterile disposable tissue grinder and homogenized for quantitative microbiology. The tube containing the ground tissue sample was filled with 5 ml 0.85% sterile saline. Five 1:10 serial dilutions were then prepared with 0.5 ml aliquots and 4.5 ml of sterile saline per aliquot. Subsequently, 0.1 ml of the homogenate and each dilution was drop plated on trypticase soy agar and placed in an incubator at 37° C. The number of viable organisms per wound was recorded as cfu/gram of tissue.

Figure 1:
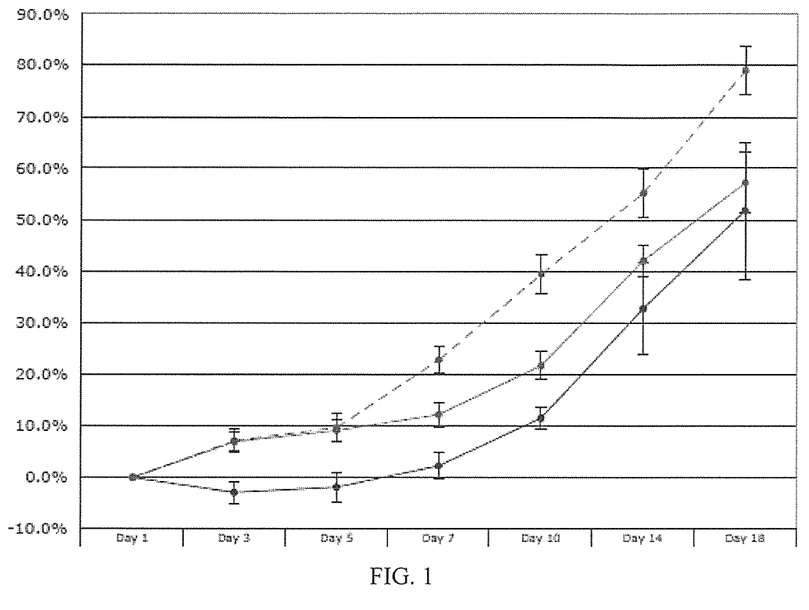
FIG. 1 shows percent wound contraction over time in a rabbit ischemic ear model. The black line (bottom) indicates the 1% DMSO control group; the red line (middle) indicates the 2% mupirocin ointment group; the purple dotted line (top) indicates the 2% 5-(2,5-bis(4-chloro-2-isopropylphenyl)thiophen-3-yl)-1H-tetrazole (w/v) in 1% DMSO (v/v) group.

5-(2,5-bis(4-chloro-2-isopropylphenyl)thiophen-3-yl)-1H-tetrazole demonstrated a >99% reduction in bacterial survival (4-log CFU drop) as compared to the control. The 5-(2,5-bis(4-chloro-2-isopropylphenyl)thiophen-3-yl)-1H-tetrazole group was significantly better than the mupirocin group in wound healing and epithelialization. The 5-(2,5-bis(4-chloro-2-isopropylphenyl)thiophen-3-yl)-1H-tetrazole group was alone among the groups in showing positive effect on erythema and edema. See FIG. 1 for a graph of percent wound reduction over time for the three groups; control group had less wound contraction than either treated group (p<0.001), and 5-(2,5-bis(4-chloro-2-isopropylphenyl)thiophen-3-yl)-1H-tetrazole treated group was better than the mupirocin treated group ($p<0.03$).

Efficacy in Cellulitis

Figure 2A:
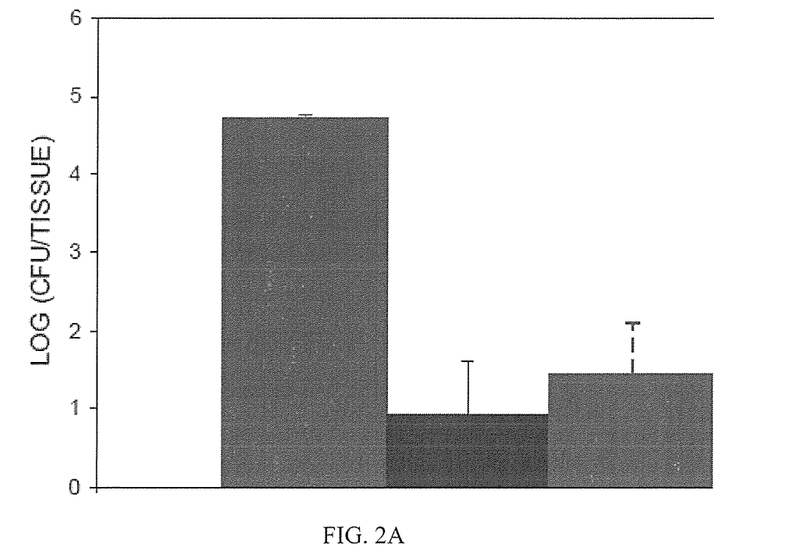
FIG. 2A shows log (colony forming units per weight of tissue) for SKH1 mice that had been intra-dermally injected with MRSA and treated for 7 days (N=5/group). Red bar (left) is control group; blue bar (middle) is comparator mupirocin treated group; green bar (right) is 5-(2,5-bis(4-chloro-2-isopropylphenyl)thiophen-3-yl)-1H-tetrazole treated group.
Figure 2B:
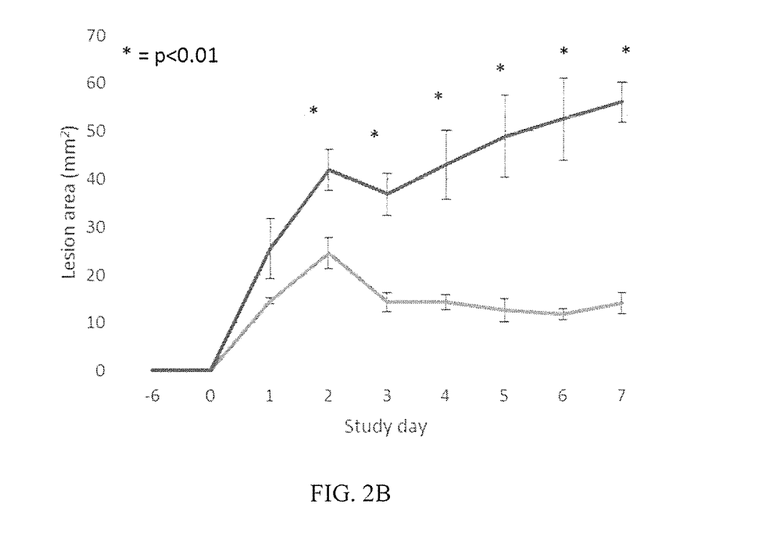
FIG. 2B shows lesion area in square millimeters for SKH1 mice that had been intra-dermally injected with MRSA and treated for 7 days (N=5/group). Dark blue line (top) is control group; light blue line (bottom) is 5-(2,5-bis(4-chloro-2-isopropylphenyl)thiophen-3-yl)-1H-tetrazole treated group.

SKH1 mice were injected intra-dermally with MRSA (N=15). 5 mice received neutral control topical formulation for 7 days. 5 mice received a topical formulation containing mupirocin for 7 days. 5 mice received a topical formulation containing 5-(2,5-bis(4-chloro-2-isopropylphenyl)thiophen-3-yl)-1H-tetrazole for 7 days. Lesion area was measured each day. After 7 days, terminal colony forming units (CFUs) were measured to determine microbiological efficacy. Treatment with 5-(2,5-bis(4-chloro-2-isopropylphenyl)thiophen-3-yl)-1H-tetrazole was found to significantly reduce lesion area and terminal CFU count (see FIG. 2B, 2A).

The invention claimed is:

1. 5-(2,5-bis(4-chloro-2-isopropylphenyl)thiophen-3-yl)-1H-tetrazole or a pharmaceutically acceptable salt thereof.

2. A pharmaceutical composition comprising 5-(2,5-bis(4-chloro-2-isopropylphenyl)thiophen-3-yl)-1H-tetrazole or a pharmaceutically acceptable salt thereof, and a dermatologically acceptable carrier.

3. A method of eradicating pathogenic bacteria within a diabetic ulcer in an individual in need of such treatment, the method comprising applying a composition comprising an effective amount of 5-(2,5-bis(4-chloro-2-isopropylphenyl)thiophen-3-yl)-1H-tetrazole upon the ulcer.

4. The method of claim 3 wherein the pathogenic bacteria is selected from the group consisting of: *Enterococcus* sp.; *Enterococcus faecalis; vancomycin resistant enterococcus* ATCC700211 and ATCC51299; *Bacillus* sp.; *Bacillus cereus; Staphylococcus* sp.; *Staphylococcus epidermidis; Staphylococcus aureus; Staphylococcus aureus* strains NRS7, NRS2, ATCC43300, NRS1, NRS382, NRS383, NRS384, MRSA clinical isolates, community-acquired MRSA clinical isolates, and multi-drug resistant (MDR) ciprofloxacin, penicillin, erythromycin and/or mupirocin resistant clinical isolates; *Streptococcus* sp.; *Streptococcus agalactiae; Streptococcus pneumoniae* and *Clostridium* spp.

5. The method of claim 3 wherein the compound is applied once or twice daily for 7-14 days or until wound contraction over time.

6. A method of treatment of diabetic foot infection in an individual in need thereof, the individual having a site of infection, the method comprising applying a composition comprising an effective amount of 5-(2,5-bis(4-chloro-2-isopropylphenyl)thiophen-3-yl)-1H-tetrazole to the site.

7. The method of claim 6 wherein the pathogenic bacteria is selected from the group consisting of: *Enterococcus* sp.; *Enterococcus faecalis; vancomycin resistant enterococcus* ATCC700211 and ATCC51299; *Bacillus* sp.; *Bacillus cereus; Staphylococcus* sp; *Staphylococcus epidermidis; Staphylococcus aureus; Staphylococcus aureus* strains NRS7, NRS2, ATCC43300, NRS1, NRS382, NRS383, NRS384, MRSA clinical isolates, community-acquired MRSA clinical isolates, and multi-drug resistant (MDR) ciprofloxacin, penicillin, erythromycin and/or mupirocin resistant clinical isolates; *Streptococcus* sp.: *Streptococcus agalactiae; Streptococcus pneumoniae* and *Clostridium* spp.

8. The method of claim 6 wherein the compound is applied once or twice daily for 7-14 days or until wound contraction over time.

9. A method of treatment of cellulitis in an individual in need thereof, the individual having a site of infection, the method comprising applying a composition comprising an effective amount of 5-(2,5-bis(4-chloro-2-isopropylphenyl)thiophen-3-yl)-1H-tetrazole to on the site.

10. The method of claim 9 wherein the pathogenic bacteria is selected from the group consisting of: *Enterococcus* sp.; *Enterococcus faecalis; vancomycin resistant enterococcus* ATCC700211 and ATCC51299; *Bacillus* sp.; *Bacillus cereus; Staphylococcus* sp.; *Staphylococcus epidermidis; Staphylococcus aureus; Staphylococcus aureus* strains NRS7, NRS2, ATCC43300, NRS1, NRS382, NRS383, NRS384, MRSA clinical isolates, community-acquired MRSA clinical isolates, and multi-drug resistant (MDR) ciprofloxacin, penicillin, erythromycin and/or mupirocin resistant clinical isolates; *Streptococcus* sp.; *Streptococcus agalactiae; Streptococcus pneumoniae* and *Clostridium* spp.

11. The method of claim 9 wherein the compound is applied once or twice daily for 7-14 days or until wound contraction over time.

12. A method of manufacture of 5-(2,5-bis(4-chloro-2-isopropylphenyl)thiophen-3-yl)-1H-tetrazole, or a pharmaceutically acceptable salt thereof, the method comprising reacting a mixture of N-protected 5-bromotetrazoles with thiophen-3-ylboronic acid under palladium cross-coupling conditions.

* * * * *